(12) United States Patent
Bonefas et al.

(10) Patent No.: US 7,692,548 B2
(45) Date of Patent: *Apr. 6, 2010

(54) METHOD AND SYSTEM FOR DETECTING OPERATOR ALERTNESS

(75) Inventors: Zachary Thomas Bonefas, Davenport, IA (US); Julian Sanchez, Bettendorf, IA (US)

(73) Assignee: Deere & Company, Moline, IL (US)

(*) Notice: Subject to any disclaimer, the term of this patent is extended or adjusted under 35 U.S.C. 154(b) by 413 days.

This patent is subject to a terminal disclaimer.

(21) Appl. No.: 11/671,293

(22) Filed: Feb. 5, 2007

(65) Prior Publication Data
US 2008/0068184 A1    Mar. 20, 2008

Related U.S. Application Data

(60) Provisional application No. 60/843,974, filed on Sep. 12, 2006.

(51) Int. Cl.
G08B 23/00    (2006.01)

(52) U.S. Cl. .................... 340/575; 340/576; 348/143; 382/117; 382/118

(58) Field of Classification Search ................ 340/575, 340/576, 439, 573.1, 540; 382/117, 203, 382/291, 2; 434/236; 351/206, 209, 246
See application file for complete search history.

(56) References Cited

U.S. PATENT DOCUMENTS

| 5,035,500 | A | 7/1991 | Rorabaugh et al. |
| 5,769,085 | A | 6/1998 | Kawakami et al. |
| 5,808,374 | A | 9/1998 | Miller et al. |
| 5,813,993 | A | 9/1998 | Kaplan et al. |
| 6,049,747 | A | 4/2000 | Nakajima et al. |
| 6,070,098 | A * | 5/2000 | Moore-Ede et al. ......... 600/544 |
| 6,580,973 | B2 | 6/2003 | Leivian et al. |
| 6,686,845 | B2 * | 2/2004 | Oyama ..................... 340/575 |

(Continued)

FOREIGN PATENT DOCUMENTS

WO    2005052878 A    9/2005

OTHER PUBLICATIONS

Ayoob, Ellen et al. Driver-Vehicle-Interface (DVI) Development of a Drowsy Driver Detection and Warning System for Commercial Vehicles. Robotics Institute, Carnegie Mellon University, Pittsburg, PA. Sep. 2005. [retrieved on Dec. 20, 2006]. Retrieved from the Internet:<URL:http://www.ri.cmu.edu/people/steinfeld_aaron.html>.

(Continued)

Primary Examiner—George A Bugg
(74) Attorney, Agent, or Firm—Yee & Associates, P.C.; Marilyn Smith Dawkins

(57) ABSTRACT

A method and system for detecting operator alertness of an operator of a vehicle or machine comprises an image collection system. The image collection system collects reference motion data associated with an operator representation when the operator is in an alert state. An image processor determines observed motion data of one or more points of a three dimensional representation of the operator during a time interval. An analyzer sends an alert signal to alert the operator if a detected angular shift of one or more points of the representation exceed a displacement threshold.

20 Claims, 9 Drawing Sheets

U.S. PATENT DOCUMENTS

| | | | |
|---|---|---|---|
| 6,925,425 B2 | 8/2005 | Remboski et al. | |
| 6,927,694 B1 * | 8/2005 | Smith et al. | 340/576 |
| 7,034,697 B2 * | 4/2006 | Oyama | 340/575 |
| 7,202,792 B2 | 4/2007 | Zhang et al. | |
| 7,423,540 B2 * | 9/2008 | Kisacanin | 340/576 |
| 2002/0015527 A1 | 2/2002 | Nambu | |
| 2002/0097160 A1 * | 7/2002 | Oyama | 340/576 |
| 2003/0123754 A1 | 7/2003 | Toyama | |
| 2003/0220814 A1 | 11/2003 | Gordon | |
| 2004/0193068 A1 | 9/2004 | Burton et al. | |
| 2005/0073136 A1 | 4/2005 | Larsson et al. | |
| 2005/0201612 A1 * | 9/2005 | Park et al. | 382/154 |
| 2006/0140510 A1 | 6/2006 | Wallace et al. | |

OTHER PUBLICATIONS

Stanford Sleepiness Scale Web Page. [retrieved on Oct. 18, 2006]. Retrieved from the Internet:<URL:http://www.stanford.edu/-dement/sss.html>.

Attention Technologies, Inc. Web Page. [retrieved on Dec. 20, 2006]. Retrieved from the Interent:<URL:http://www.attentiontechnology.com/pro.html>.

Web Page Advertisement for "Seeing Machines". [retrieved on Dec. 20, 2006] Retrieved from the Internet:<http://www.seeingmachines.com/facelab.htm>.

Grace, Richard et al. The Carnegie Mellon Trucksim: A Tool To Improve Driving Safety. pp. 135-1 through 135-8. Published by IEEE 1998.

Freund, Deborah et al. A Holistic Approach to Operator Alertness Research. Presented Jan. 22-28, 1995 in Washington, D.C. at the 74th Annual Meeting of the Transportation Research Board.

Federal Motor Carrier Safety Administration. Commercial Motor Vehicle/Driver Fatique and Alertness Study. [retrieved on Oct. 18, 2006]. Retrieved from the Internet:<URL:http://www.fmcsa.dot.gov/facts-research/research-technology/publications/cmvfatiquestudy.htm>.

Stern, John A. et al. The Eye Blink and Workload Considerations. Proceedings of the Human Factors Society—28th Annual Meeting—1984, pp. 942-944.

Delphi Continues to Up-Integrate Safety Systems to Bring Down Total Cost. [online]. Delphi Press Releases Oct. 18, 2006. [retrieved on May 22, 2007]. Retrieved from the Internet:<URL: http://delphi.com/news/pressReleases/pressReleases_2006/pr_2006_10_18_001/>.

EP Search Report for EP07116114 dated Dec. 9, 2009.

* cited by examiner

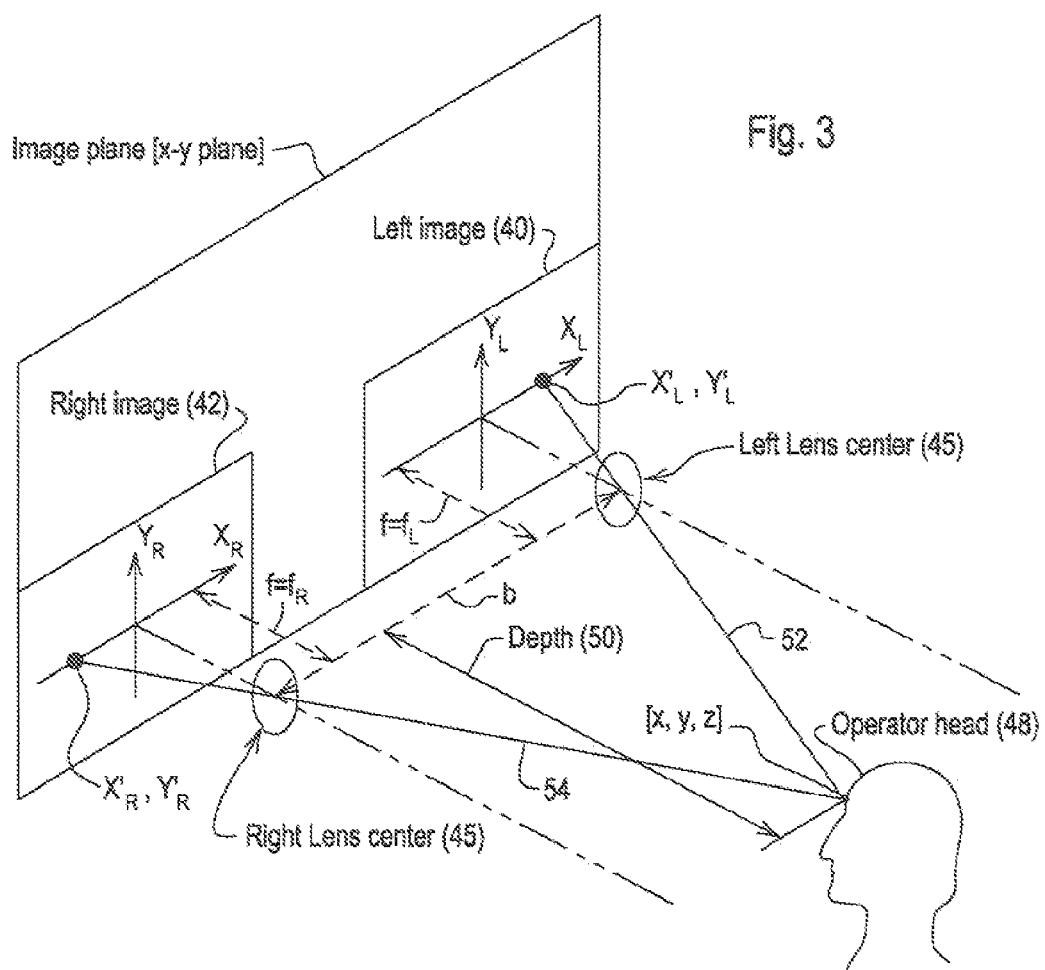

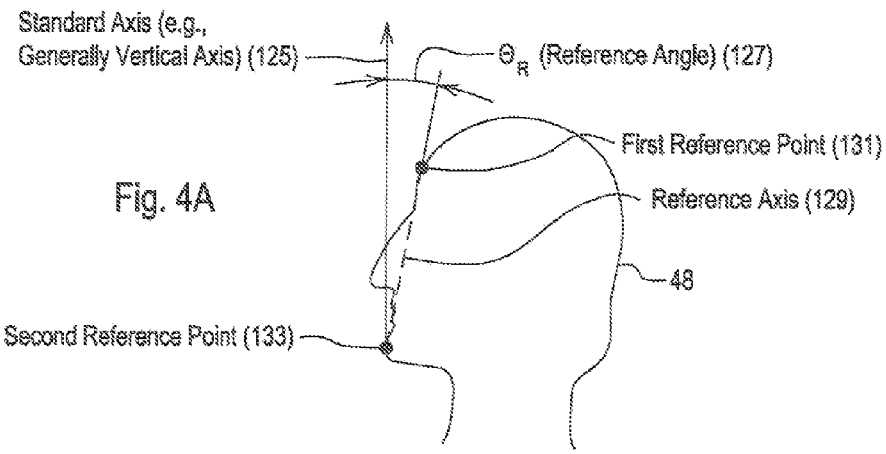
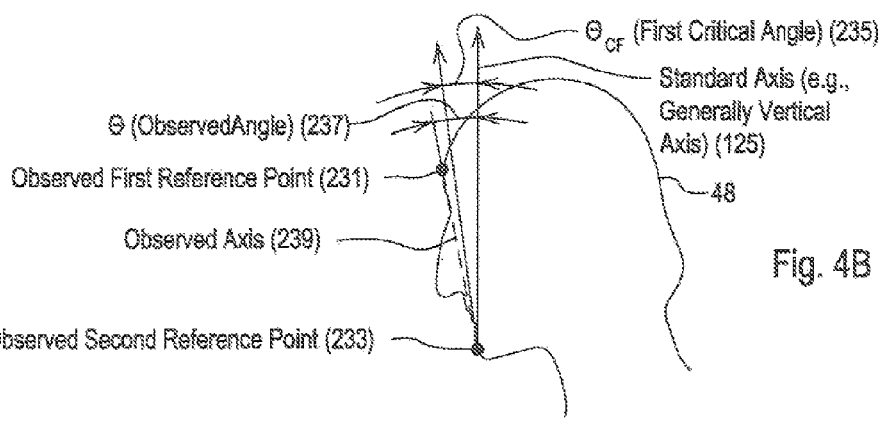
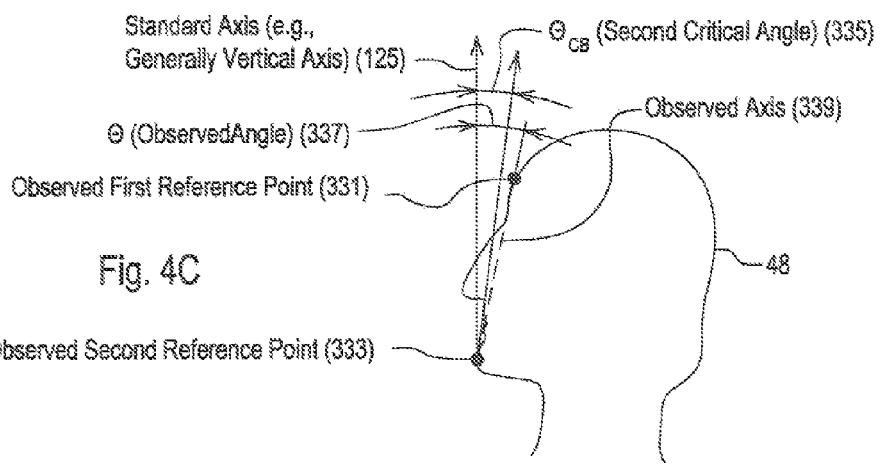

METHOD AND SYSTEM FOR DETECTING OPERATOR ALERTNESS

This document (Including the drawings) claims priority based on U.S. provisional Ser. No. 80/843,974, filed Sep. 12, 2006, and entitled METHOD AND SYSTEM FOR DETECTING OPERATOR ALERTNESS, under 35 U.S.C. 119(e).

FIELD OF THE INVENTION

This application relates to a method and system for detecting operator alertness using stereo vision.

Monocular machine vision may offer limited capability in detecting operator alertness. The position or movement of an operator may be detected by analyzing a monocular image. However, monocular vision data may be deficient in providing reliable determination of the position or movement of an operator, which may require depth perception to ascertain the three dimensional characteristics of the position or movement of an operator. Operator alertness systems that rely on observation of the eyes of an operator encounter technical difficulties where the operator does not constantly face in a uniform direction (e.g., forward) or where the operator wears eyeglasses. Thus, there is need for a method and system for detecting operator alertness using stereo vision.

SUMMARY OF THE INVENTION

In accordance with one aspect of the invention, a method and system for detecting operator alertness of an operator of a vehicle or machine comprises an image collection system. The image collection system collects reference position data or reference motion data associated with an operator, or a portion thereof when the operator is in an alert state. An image processor determines observed position data or observed, motion data of one or more points of a three dimensional representation of the operator during a time interval. An analyzer sends an alert signal to alert the operator if a detected angular shift of one or more reference points of the representation exceed a displacement threshold, or motion threshold.

BRIEF DESCRIPTION OF THE DRAWINGS

FIG. 3 shows a diagram that illustrates the collection of stereo vision data and determination of three-dimensional world coordinates for one or more points associated with an operator, or portion thereof.

FIG. 4A shows a profile of an operator's head in a position that indicates an alert state of an operator.

FIG. 4B and FIG. 4C show a profile of an operator's head in a position that indicates an inattentive state of an operator.

Like reference numbers in different drawings indicate like elements, steps or procedures.

DESCRIPTION OF THE PREFERRED EMBODIMENT

Figure 1A:
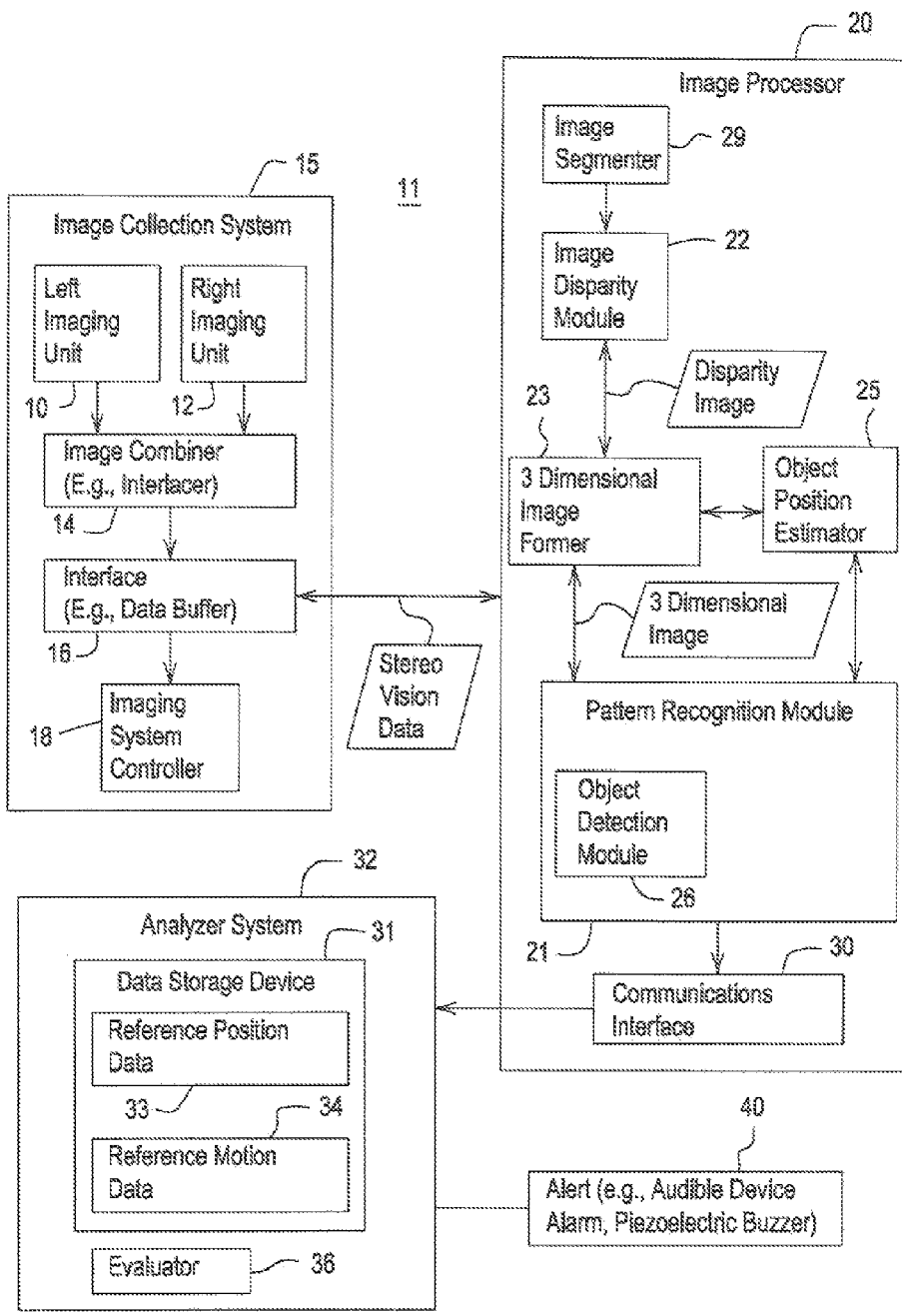
FIG. 1A is a block diagram of one embodiment of a system for detecting operator alertness using stereo vision in accordance with the invention.

In accordance with one embodiment, FIG. 1A illustrates a detection system 11 for detecting an alertness or inattentiveness of an operator. As used herein, the operator generally refers to the operator of any vehicle or any machine. The vehicle may comprise any train, bus, airplane, aircraft, helicopter, ship, boat, watercraft, automobile, truck, tractor, combine, agricultural equipment, construction equipment forestry equipment, earth-moving machinery, mining equipment, or the like. The vehicle may have, but need not have, unmanned, semi-autonomous, or autonomous capabilities with respect to guidance and navigation. For example, the vehicle may have a guidance system that uses a location-determining receiver (e.g., a Global Positioning System receiver with differential correction) to determine a location of a vehicle to facilitate-guidance of a vehicle in accordance with a path plan.

The detection system 11 comprises an image collection system 15 coupled to an image processor 20. In turn, the image processor 20 is coupled to an analyzer 32. The analyzer 32 may provide a control signal to an alert device 40.

Image Collection System

The image collection system 15 comprises a left imaging unit 10 and a right Imaging unit 12 that are coupled to an image combiner 14 (e.g., an interlacer). The image combiner 14 may be coupled to an interface 16. The interface 18 provides a communications interface (or a data buffer) for the stereo vision data transmitted from the image collection system 15 to the image processor 20. An imaging system controller 18 may control the optical characteristics of the left imaging unit 10, the right imaging unit 12, or the format of stereo vision data or image data outputted by the interface 16, for example.

The optical characteristics of the imaging units (10, 12) may include any of the following: the aperture of one or both imaging units (10,12), the effective or actual focal length of one or both imaging units (10,12), lens parameters of one or both imaging units (10,12), the sensitivity to luminance and frequency response of one or both imaging units or their components (e.g., charge coupled devices (CCD) or other detectors), resolution of one or both imaging units (10, 12) (e.g., expressed as number of pixels per image or pixel dimensions) and filtering of the output of one or both imaging units (10,12) for noise, optical distortion, chrominance distortion, luminance distortion, or for lighting variations (e.g., shade versus sunlight). The frequency response of one or both imaging units (10, 12) may support the collection of images in the following frequency spectrum of the electromagnetic spectrum: humanly visible light, a portion of the visible light spectrum (e.g., red light spectrum, green light spectrum and blue light spectrum or other color portions of the humanly visible light spectrum), near-infrared frequency range, the infrared frequency range, a thermal frequency spectrum, and any combination of the foregoing frequency ranges.

The left imaging unit 10 and right imaging unit 12 gather a pair of raw stereo scene images of the scene or operator, or a portion thereof, within the scene from spatially offset perspectives at a common time. The imaging units (10,12) may be mounted within a cab, cabin, bridge, or cockpit of a vehicle or externally such that an operator, or a portion thereof, within the cab, cabin, bridge, or cockpit is visible, or within the field of view of the imaging units (10,12). The portion of the operator that is captured or visible in the collected image data or stereo image data may include any of the following: the operator's head, a profile of the operator's head, the operator's face, a profile of the operator's face, the operator's head, the operator's neck, the operator's bust, the operator's facial features, the operator's hair, the operator's forehead, and the operator's chin.

The left imaging unit 10 and the right imaging unit 12 are offset by a fixed, known spatial amount, which may be referred to as the stereo baseline. The image combiner 14 combines the raw stereo scene images to produce composite image data or a composite data stream. For example, the composite data stream or stereo vision data may consist of alternating frames, alternating lines of frames, alternating words, bytes, bits, or data packets of left image data from the left imaging unit 10 and right image data from the right imaging unit 12, in one embodiment, the image combiner 14 comprises an interlace that accepts an input of a left image data stream and a right image data stream and provides an output of an interlaced data stream that contains bytes from both the left image data stream and the right image data stream. The image collection system 15 supports synchronization of images collected from the left imaging unit 10 and the right imaging unit 12 such that images captured at the substantially the same time are associated with one another. The image collection system 15 and/or the system 11 is well suited for mounting in any location (e.g., an inconspicuous location) within the cab or cockpit of a vehicle, and need not be mounted in alignment with the eyes of the operator to capture the status of the operator's eyes, unless eye monitoring for alertness is desired.

Image Processor

The image processor 20 comprises an image segmenter 29, an image disparity module 22, a three dimensional image former 23, an object position estimator 25, a pattern recognition module 21, and a communications interface 30. In one embodiment, the image segmenter 29 communicates with the image disparity module 22. The image disparity module 22 communicates with the three dimensional image former 23. In turn, the three-dimensional image former 23 communicates with the object position estimator 25, the pattern recognition module, 21, or both. The pattern recognition module 21 communicates with the communications interface 30. The communications interface 30 is an intermediary that manages communications between the image processor 20 and the analyzer 32.

In one embodiment, the image processor 20 facilitates the determination of a range of the operator, or portion thereof, with respect to the image collection system 15 and the dimensions of an operator, or portion thereof. The image processor 20 is well suited for creating a three dimensional representation of the operator, or portion thereof, or a scene based on the disparity map image and the stereo vision data. However, to conserve data processing and computational resources, the image segmenter 29 may extract or segment operator-related image data from the scene image data or background image data (e.g., cockpit, cabin or cab image data) The image segmenter 29 provides the extracted operator-related image data to the image disparity module 22. Operator-related image data may refer to image dais that is a volume or region of the scene that is likely to contain the operator, or a portion thereof, of image data that meets a test (e.g., color similarity or differentiation) that is probative of whether the image data is related to the operator. If the image segmenter 29 overinclusively extracts operator-related image data that includes background data, additional data processing resources of the system (11 or 111) may be used.

The image disparity module 22 creates a disparity map image that represents disparity between the raw stereo scene images from the left imaging unit 10 and the right imaging unit 12. The disparity map may be based on raw stereo images, operator-related image data, or both. The three-dimensional image former 23 accepts an input of a disparity image or other stereo vision image data (e.g., interlaced data stream) of a scene (or operator, or portion thereof) and produces a three-dimensional representation of the scene (or operator, or portion thereof) as an output.

In one embodiment, the three dimensional image former 23 may create or form a three-dimensional image representation of the operator, or a portion thereof, based on one or more of the following types of input data: the disparity image, raw left image data, and raw right image data, stereo vision data, and interlaced image data. The three-dimensional representation may comprise a constellation of data points that lie on the surface of the operator, or a portion thereof; a framework of planar patches or a grid that lie on the surface of the operator, or a portion thereof; a rough block or cubic representation of the dimensions of the operator, a portion thereof; or another three-dimensional model of the operator. The data points on the operator, the framework that models the operator, or another three-dimensional model may be referenced to a stationary observation point of the image collection system 15 or otherwise.

The object position estimator 25 may determine or estimate one or more of the following: (1) the range (depth 50) of the operator, or a portion thereof, from the Image collection system 15 or a reference point associated therewith, (2) the three-dimensional dimensions of the operator, a portion thereof, (e.g., width, depth and height), (3) two-dimensional dimensions of the operator, or a portion thereof, (e.g., width and length) and range to the operator; (4) an estimated center of mass or geometric center of the operator, or a portion thereof; (5) a reference axis associated with the operator's head, where the reference axis is defined by at least two reference points lying on or within the operator's head, and their respective three dimensional coordinates when the operator is in an alert state, (6) a reference axis associated with the operator's head, where the reference axis is defined by a first reference point associated with the operator's forehead and a second reference point associated with the operator's chin when the operator is in an alert state, (7) an observed axis associated with the operator's head, where the observed axis is defined by at least two reference points lying on or within the operator's head, and their respective three dimensional coordinates, when the operator is in any state (alert or not), (8) an observed axis associated with the operator's head, where the reference axis is defined by a first reference point associated with the operator's forehead and a second reference point associated with the operator's chin when the operator is any state (alert or not), and (9) any angular displacement or tilt between a reference axis and an observed axis.

The range of the object may represent the distance between a surface point on the operator and a reference point associated with the imaging collection system 15 (e.g., a baseline of the imaging units (10, 12)). In an alternative embodiment, the range of the operator may represent the distance between a geometric center or center of mass of the operator and the imaging collection system 15 or a reference point associated therewith. In yet another alternate embodiment, the range of the operator may represent the distance between a reference point associated with the imaging collection system 15 and some reference point that lies on or within the operator.

The pattern recognition module 21 or object detection module 28 communicates with one or more of the following components: the object position estimator 25 and the three dimensional image former 23. The pattern recognition module 21 comprises an object detection module 26, which facilitates identification of an operator, or a portion thereof, within a scene, collected image data or collected stereo vision data. The pattern recognition module 21 may facilitate the identification of an operator, or portion thereof, in a scene from stereo image data and the extraction of an operator-related image data from background image data within the Stereo vision data based on one or more of the following: (1) color information (e.g., pixels or voxels) associated with the image, (2) luminance information (e.g., pixels or voxels), associated with the image, (3) three-dimensional shape data on the operator, or any portion thereof, and (3) dimensions of the operator, or any portion thereof. For example, an operator, or portion thereof, may have a generally uniform color (e.g., skin color, flesh color, facial feature colors, hair color, hat color, eyeglass frame color, clothing color) which is distinct from the background data or a particular luminance value of pixels that is distinct from the background data. A voxel refers to a volume pixel or pixel of a three-dimensional image.

In one configuration, the object detection module 26 may differentiate an operator, or portion thereof, from the background or remainder of an image by one or more of the following techniques: (1) identifying operator-related image portions by matching color parameters of pixels (or voxels) in an image or portion of an image to reference color parameters of pixels (or voxels) within one or more depth zones or a three-dimensional image, where the reference color parameters represent expected color parameters for the operator (e.g., skin color, hair color, facial features of the operator), (2) identifying operator-related image portions by matching observed size parameters to a reference object profile size (e.g., typical dimensions of operators, heads, necks, busts, and facial features) within one or more depth zones of a three-dimensional image, and (3) rejecting or filtering put image portions associated with color parameters or pixels that are consistent with reference color parameters of an interior of a cab, cabin, or cockpit of a vehicle. The reference color parameters of each particular operator may be obtained from the image collection system 15 operating under defined lighting and head position conditions, whereas the reference color parameters of the cab, cabin or cockpit may be obtained from the image collection system 15 when the cab, cabin or cock pit is empty, or otherwise.

The communications interface 30 communicates pattern recognition data, row location data, operator location data, operator avoidance data, operator dimension data, and operator range data to an analyzer 32.

Analyzer

The analyzer 32 comprises a data storage device 31 and an evaluator 36. The data storage device 31 stores reference position data 33 and reference motion data 34. The reference position data 33 may comprise position or three dimensional coordinates, of one or more reference points associated with an operator, or a portion (e.g., operator's head, neck, face, or bust) thereof. For example, the reference position data may represent a reference axis defined by two reference points lying on a surface of the operator's head, and their respective three dimensional coordinates, when the operator is in an alert state. The reference motion data may comprise a change in position versus time of one or more reference points. Each reference point may be expressed in three dimensional coordinates, or otherwise consistent with the reference position data.

The observed position data may comprise position or three dimensional coordinates of one or more reference points associated with an operator, or a portion (e.g., operator's head, neck, face, or bust) thereof. For example, the observed position data may represent a reference axis defined by two reference points lying on a surface of the operator's head, and their respective three dimensional coordinates, when the operator is in an alert state. The observed motion data may comprise a change in position versus time of one or more reference points. Each reference point may be expressed in three dimensional coordinates, or otherwise consistent with the observed position data.

Alert Device

The alert device 40 may comprise an alarm, a siren, a buzzer, an audible oscillator, a flashing light, a light, a light-emitting diode, a display, a liquid crystal display, a switch, relay or semiconductor that triggers an electronic device (e.g., a radio or a volume control), a vibrating device, a piezoelectric-transducer, or another device to alert, stimulate, or wake the operator, to prevent drowsiness, or to otherwise discourage instinctiveness. For instance, a vibrating device or piezoelectric transducer may be associated with the steering wheel or the operator's seat to vibrate the steering wheel or the operator's seat in response to a triggering signal or alert signal from the analyzer system 32.

Figure 1B:
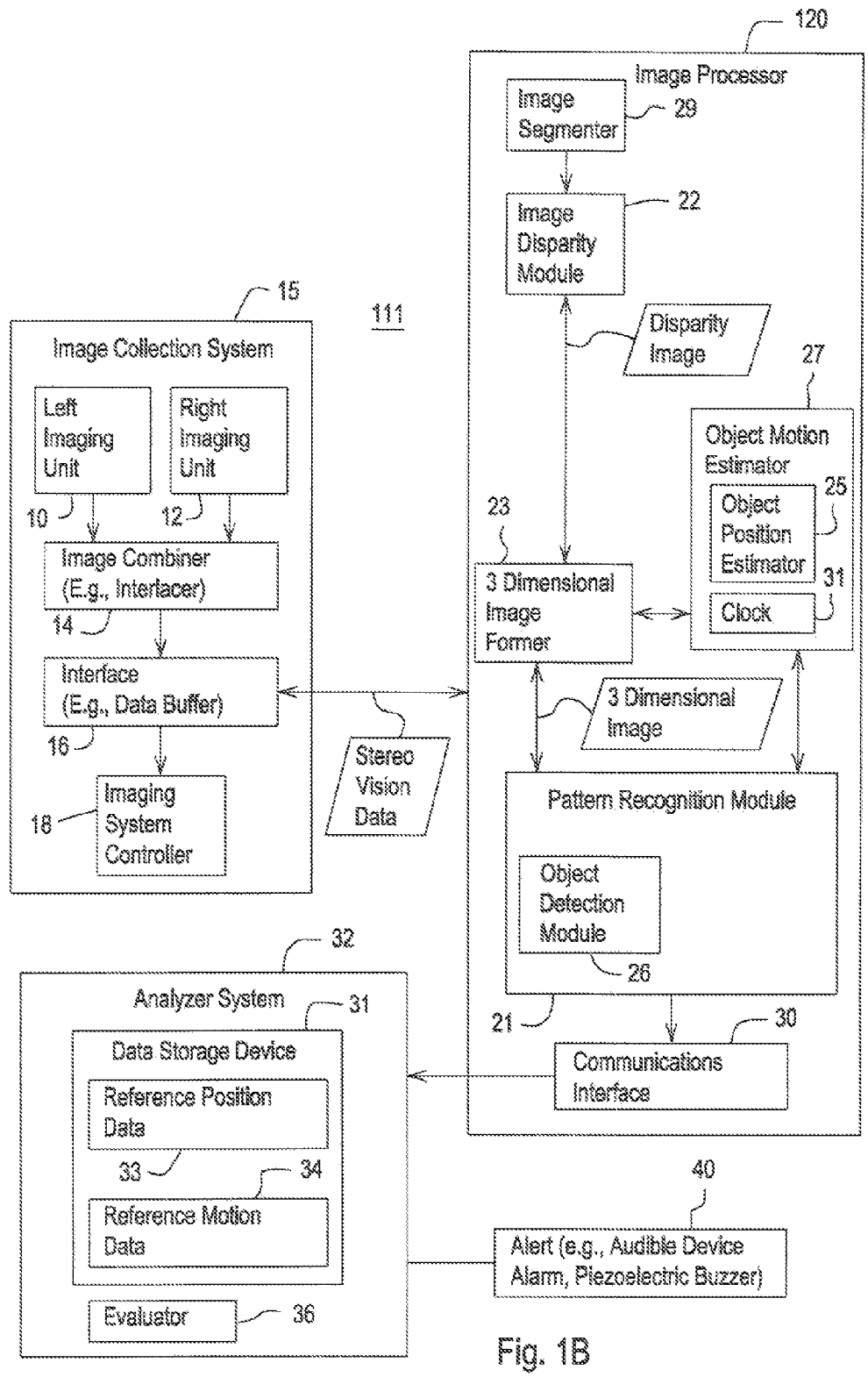
FIG. 1B is a block diagram of another embodiment of a system for detecting operator alertness-using stereo vision in accordance with the invention.

The system of FIG. 1B is similar to the system of FIG. 1A, except the system of FIG. 1B further comprises a motion position estimator 27.

The motion position estimator 27 comprises the combination of an object position estimator 25 and a clock 31 (e.g., or timer) to determine or estimate one or more of the following: (1) whether the operator, or portion thereof, is stationary or moving (e.g., rotating or tilting), (2) whether the reference axis or the observed axis (associated with the operator) is stationary or moving (e.g., rotating or tilting), (3) whether one or more reference points associated with the operator, the operator's head, the operator's neck or otherwise is stationary or moving, (4) the velocity, acceleration, speed, or heading of the operator, or any portion thereof, relative to the imaging collection system 15 or another stationary reference point, (5) the velocity, acceleration, speed, angular velocity, angular acceleration, rotational displacement, or heading of reference points, a reference axis, or an observed axis relative to the imaging collection system 15 or another stationary reference point and (6) any motion data related to the position data provided by the object position estimator 25. For the configuration of FIG. 1B, the pattern recognition module 21 or object detection module 26 communicates with one or more of the following components: the object position estimator 25, the object motion estimator 27, and the three dimensional image former 23.

Figure 2:
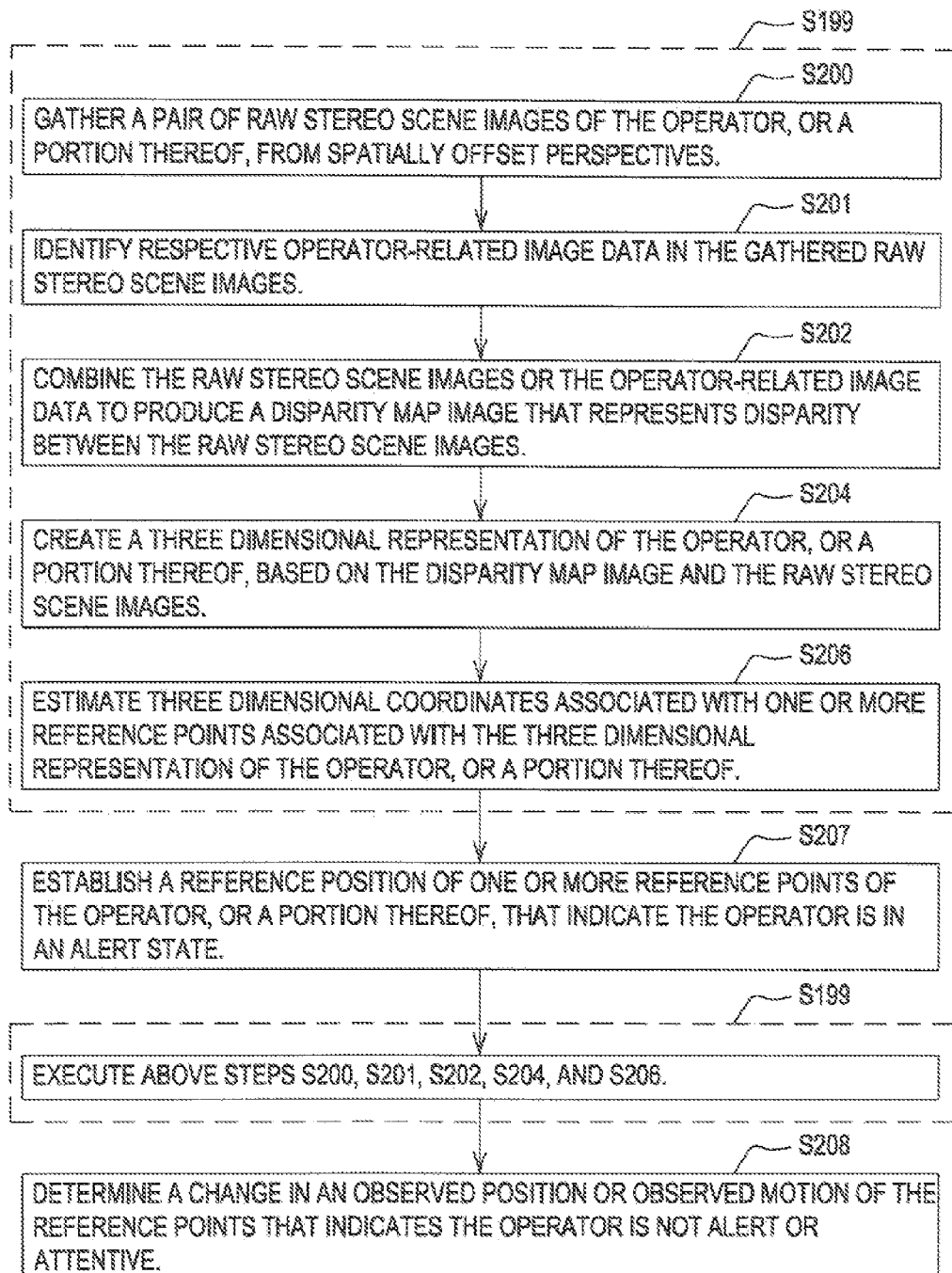
FIG. 2 is a flow chart that generally illustrates a first embodiment of a method for detecting operator alertness.

FIG. 2 generally describes a method for defecting operator alertness or inattentiveness for an operator of a vehicle or machine. The method of FIG. 2 begins in step S200.

In step S200, the image collection system 15 gathers (e.g., simultaneously gathers) a pair of raw stereo scene images of the operator, or a portion thereof, from spatially offset perspectives. The spatially offset perspective is preferably one in which the focal axis of the first imaging unit 10 and the second imaging unit 12 are separated by a known distance and orientation (e.g., fixed linear distance called stereo baseline b in FIG. 3).

In step S201, an image processor 20 or image segmented 29 identifies an operator related image data in the gathered stereo scene images. For example, the image processor 20 or the image segmenter 29 identifies operator-related image data by analyzing one or more images in color space. The image processor 20 or the image segmenter 29 may identify, extract, distinguish or discern the operator-related image data from the background data of the image data in color space by applying one or more of the following techniques to the image or a portion of an image: color differentiation, color histogram analysis, probability density function analysis, and edge analysis in an image region within the boundaries of the operator and immediately outside the boundaries of the operator, in one embodiment, to differentiate the operator from the background of the image or scene (e.g., interior of the cab or cockpit), the image segmenter 29 or image processor 20 may apply data processing resources of the image processor 20 first to a candidate region of the scene where the operator is supposed to be seated and secondarily to the entire field of view of the image collection system 15.

To accordance with a first technique for executing step S201, the image processor 20 or the image segmenter 29 compares a collected derivative data set of the collected image to a reference derivative data set of a reference image. In one embodiment, the collected derivative data set may represent a probability density function or a color histogram analysis applied to a collected image or a portion thereof. Further, the reference derivative data set of a reference image may be defined as a probability density function of color parameters (e.g., color, tone, hue, or intensity) or color histogram of color parameters derived from one or more reference images (e.g., of the operator in interior of the cockpit or cab of the vehicle). The reference image may be taken at regular intervals or each time a vehicle is started or used, for example.

In accordance with a second technique for executing step S201, the image processor 20 or the image segmenter 29 identifies the presence of an operator, or portion thereof, in (pixels or voxels of) the collected image with one or more colors or color attributes (e.g., flesh tone, skin tones or hair color) that are sufficiently distinct to a particular corresponding operator. Where a portion of the (pixels or voxels) of the collected image has colors substantially match or are sufficiently correlated to the reference image, the operator, or a portion thereof, is identified as present. In one embodiment, the image processor 20 or object detection module 25 identifies the outline, object boundary, or edges of the object or operator by distinguishing the operator color of the operator from the background color of a background image data or distinguishing a material color transition between the boundary of the operator and the background through comparisons of groups of pixels or voxels in the region of the image.

Advantageously, in step S201 the application of color differentiation, color probability density function, histogram and edge analysis may be completed rapidly to identify operators, or portions thereof, in a structured environment, such as within a cab or cockpit of a vehicle.

In step S202, an image disparity module 22 or image processor 20 combines raw stereo scene images or operator-related image data to produce a disparity map that represents disparity between the raw stereo scene images collected in step S200. The raw stereo images may be expressed as or converted into greyscale images as inputs to the disparity module 22. The disparity module 22 uses a disparity algorithm (e.g., correlation of common points in each raw stereo image or a sum of absolute differences applied to such common points) to form a disparity map based on a spatial relationship between each point in one raw stereo image its corresponding point in the other stereo image. The disparity module creates a disparity map for each pixel in one of the raw stereo scene images. The disparity map may be stored as a single greyscale image or a monochrome image in which disparity is a function of x and y in one raw stereo scene image or d (x,y), for example.

Stereo disparity (d) is inversely proportional to the depth of an operator. The stereo disparity (d) is defined as $d=bf/z$, where b is the stereo baseline, f is the focal length of the imaging units (10 and 12), and z is the depth of an operator from the imaging units (10 and 12). The disparity map is a representation that facilitates the removal of some redundant data from the two raw stereo images collected in step S200.

In step S204, the three dimensional image former 23 or the image processor 20 creates a three-dimensional representation of the scene, the operator, or a portion thereof, based on the disparity map image and at least one of the raw stereo scene images gathered in step S200. In one example for carrying out step S204, the three dimensional image former 23 may accept an input of the disparity map, which has information about x,y,d for the scene or an operator, and map the x,y,d information to x,y,z coordinates for the scene or any operator in the scene.

In another example for carrying out step S204, the three dimensional image former 23 extracts the three-dimensional map from the disparity map and at least one of the raw stereo scene images through (a) the application of the stereo vision equations discussed in more detail in FIG. 3 to estimate the three-dimensional real world coordinates of the operator from the perspective of the imaging system and (b) construction of a surface model of the operator based on the estimate of three dimensional world coordinates.

The construction of the surface model may use a grid of voxels that generally defines the three-dimensional shape of an operator to form or interconnect the nearest neighbor points with linear segments or tangent planar grids, for example. Although greater resolution of the surface model of the operator is useful for operator classification or the application of pattern recognition techniques, the surface model can be crude to produce a rapid surface solution for detecting the position or motion of one or more of the following: an operator, an operator's head, an operators neck, an operator's bust, any reference points lying within or one surface associated with the operator, and any reference points lying within or on any portion of the operator.

In step S206, an object position estimator 25 or image processor 20 estimates three dimensional coordinates associated with one or more points of the three dimensional representation. For example, the depth (d) of the operator, or a portion thereof, is estimated by correlation of common data points in the limited region of the operator in a left image and a corresponding right image of a stereo image. Once the depth is available, real world y data within the limited region of the outline, boundary or edges of the operator, or a portion thereof, may be computed by reference to either the right image or the left image. By processing only a limited region within the outline, boundary or edges of the operator, the data processing resources are minimized and time reduced to practice the method of FIG. 2.

In step S208, to reduce computational time and data processing resources, the image processor 20 or object defection module 26 limits the analysis or image processing to any of the following: (1) a particular region of depth of a three-dimensional image, (2) a two dimensional depth slice of uniform depth of three-dimensional image, (3) an image (e.g., a two-dimensional image) from one of the imaging units (19 or 12).

In to step S207, the image collection system 15 collects one or more reference images (e.g., stereo vision data) of the operator, an operator's head region, another portion of the operator. The image processor 20 uses the reference image or images to establish a reference position of one or more reference points of the operator or a portion thereof to indicate the operator is in an alert state. The reference image may be taken when the operator is generally alert or attentive, for example.

Steps S200, S201, S202, S204, and S208 shall be collectively known as step S199, which relates to a stereo vision imaging process. During the previous execution of steps S200, S201, S202, S204, and S206, the steps were executed in preparation for establishing the reference position in step S207. After step S207, step S199 or the stereo vision imaging process is executed in preparation for determining a change in observed position or observed motion in step S208.

In step S208, the analyzer 32 or image processor 20 determines a change In an observed position of the reference points or a change in observed motion of the reference points that indicates an operator is not alert or attentive. For example, the reference points of the operator, or a portion thereof, may shift from the established reference position to an observed reference position that indicates that the operator is inattentive, asleep, unconscious, or otherwise not alert.

FIG. 3 is an illustration of a typical representation of how three-dimensional information on an object or operator representation is extracted from an image collection system 15 that collects stereo vision images. An operator, or a portion thereof, may be regarded as an object in the collected image data, stereo vision data, operator-related image data, or the like. The operator-related image data may relate to or define one or more of the following: an operator, an operator's head, an operator's face or portion thereof, an operator's nose, an operator's forehead, an operator's chin, an operator's mouth, a operator's facial feature, an operator's neck, an operator's hair or hat, an operator's clothing, and an operator's bust.

A right lens center 45 and a left lens center 44 are associated with the right imaging unit 12 and the left imaging unit 10, respectively. The right lens center 45 and left lens center 44 may represent central regions of the lenses of the imaging units. A dashed reference line, labeled "b" for stereo baseline b, interconnects the right lens center 45 and the left lens center 44. The first imaging unit 10 and the second imaging unit 12 are separated by a distance associated with the stereo baseline (b). The optical axes of each imaging unit is perpendicular to the stereo base Sine. An operator head 48 is separated from baseline b by a depth 50. A group of points on the operator head 48 may be expressed as three dimensional information that defines the shape, size, and spatial dimensions of the operator head 48.

The three-dimensional information may be represented in a Cartesian coordinate system, a polar coordinate system, a spherical coordinate system, or otherwise. As illustrated in FIG. 3, the three dimensional information is expressed in accordance with Cartesian coordinates. For example, the three dimensional information may include coordinate values (e.g., x, y, z) for each point on the surface of the operator head 48. As illustrated in FIG. 3, the three dimensional information is referenced to an x-y image plane generally parallel to base line b of the imaging units (10 and 12). A z-axis is perpendicular to or normal to the x-y image plane.

The left image 40 and the right image 42 lie in the image plane (i.e., the x-y plane) in FIG. 3. The left image 40 represents a view of the operator head 48 (and surrounding image) from the perspective of the left imaging unit 10, which includes the left lens center 44. The right image 42 represents a view of the operator representation 48 (and surrounding image) from the perspective of the right imaging unit 12, which includes the right lens center 45. The right image 42 lies behind the right lens center 45 by a focal length, designed $f_r$; the left image 40 lies behind the left lens center 44 by a focal length designated $f_l$. A left image coordinate system is defined on the left image plane as $x_l$, $y_l$. A right image coordinate system is defined on the right image plane, as $x_r$, $y_r$.

The three dimensional world coordinates of a point in a scene or on an object (e.g., operator or head) in the scene are as follows:

$$x = \frac{b(x'_l - x'_f)}{2d},$$

$$y = \frac{(y'_l - y'_r)}{2d},$$

and $$z = \frac{bf}{d}$$

where b is the stereo baseline distance between the optical centers of the two imaging units, d is the disparity, which is $x'_l - x'_r$, and f is the effective focal length of the imaging units for the case where $f=f_r$, $f_l$, $x'_l$ is the $x_l$ coordinate on the left image of the image plane corresponding to the point on the object, $y'_l$ is $y_l$ coordinate on the coordinate on the left image plane, $x'_r$ is the $x_r$ coordinate on the right image of the image plane corresponding to the point on the object, and $y'_r$ is $y_r$ coordinate on the coordinate on the right image plane. The z dimension is synonymous with the depth of a point on the object.

The above equations may be applied repeatedly (e.g., periodically or at regular intervals or sampling times) during operation of the vehicle. As the operator alertness system (11 or 111) moves throughout a work area or its environment to capture a group of stereo scene images of an operator head 48. Periodically or at regular time intervals, additional stereo images may be collected to extract further three-dimensional information on the same operator, or portion thereof, to detect any changes over time that may indicate an operator's level of alertness. Accordingly, a three-dimensional reconstruction of the dimensions and range of operator, or portion thereof, may be based on three dimensional image points calculated at different times and registered to a common reference or coordinate system with respect on one another. Registration of different stereo images taken at different times may be accomplished by selecting portions of the scenes and matching for luminance, color or intensity of the pixels or voxels. Corresponding luminance values, and color values (e.g., in RGB color space, or otherwise) may be associated with each data point to form a voxel or another multidimensional representation.

FIG. 4A shows a profile of an operator or operator head 48 in a position that indicates an alert state of an operator. A reference axis 128 is defined by a first reference point 131 and second reference point 133 associated with a head of an operator in a position that indicates an alert state. For example, the first reference point 131 may lie on a forehead or other surface of the operator head 48, whereas the second reference point 133 may lie on a chin of the operator head 48.

The reference axis 129 may have a reference angle 127 (also referred to as $\theta_R$) to a standard axis 125 of known orientation or generally vertical axis.

FIG. 4B and FIG. 4C show a profile of an operator head 48 in a position that indicates an inattentive state of an operator. Like reference numbers in FIG. 4A, FIG. 4B and FIG. 4C indicate like elements.

In FIG. 4B, the operator head 48 is tilted forwards by an amount which exceeds a displacement threshold (e.g., critical angle), which is potentially indicative of or correlated to an operator that is not in an alert state, in FIG. 4B, the operator head 48 is tilted toward by an observed angle 237 (which is also labeled θ) that exceeds a displacement threshold (e.g., first critical angle 235, which is also labeled $\theta_{CF}$). Because the observed angle 237 exceeds the first critical angle 235, the detection system (11 or 111) indicates that an Operator that is not in an alert state and may trigger the issuance of an alarm via alert device 40.

The observed angle 237 relates to the angle formed between the standard axis 125 (e.g., generally vertical axis) and the observed axis 239. The observed axis 239 is defined by a first reference point 231 and a second reference point 233. The observed first reference point 231 is on the same position (e.g., operator's forehead) of the operator head 43 as the first reference point 131, but is displaced in absolute three dimensional coordinates. Similarly, the observed second reference point 233 is on the same position (e.g., operator's chin) of the operator head 48 as the second reference point 133, but is displaced in absolute three dimensional coordinates.

In FIG. 4C, the operator head 48 is tilted backwards by an amount which exceeds a displacement threshold (e.g., critical angle), which is potentially indicative of or correlated to an operator that is not in an alert state. In FIG. 4C, the operator head 48 is tilted forward by an observed angle 337 (which is also labeled θ) that exceeds a displacement threshold (e.g., second critical angle 335, which is also labeled $\theta_{CB}$). Because the observed angle 337 exceeds the second critical angle 335, the detection system (11 or 111) indicates that an operator that is not in an alert state and may trigger the issuance of an alarm via alert device 40.

The observed angle 337 relates to the angle formed between the standard axis 125 (e.g., generally vertical axis) and the observed axis 339. The observed axis 339 is defined by a first reference point 331 and a second reference point 333. The observed first reference point 331 is on the same position (e.g., operator's forehead) of the operator head 48 as the first reference point 131, but is displaced in absolute three dimensional coordinates. Similarly, the observed, second reference point 331 is on the same position (e.g., operator's chin) of the operator head 48 as the second reference point 333, but is displaced in absolute three dimensional coordinates.

Figure 5:
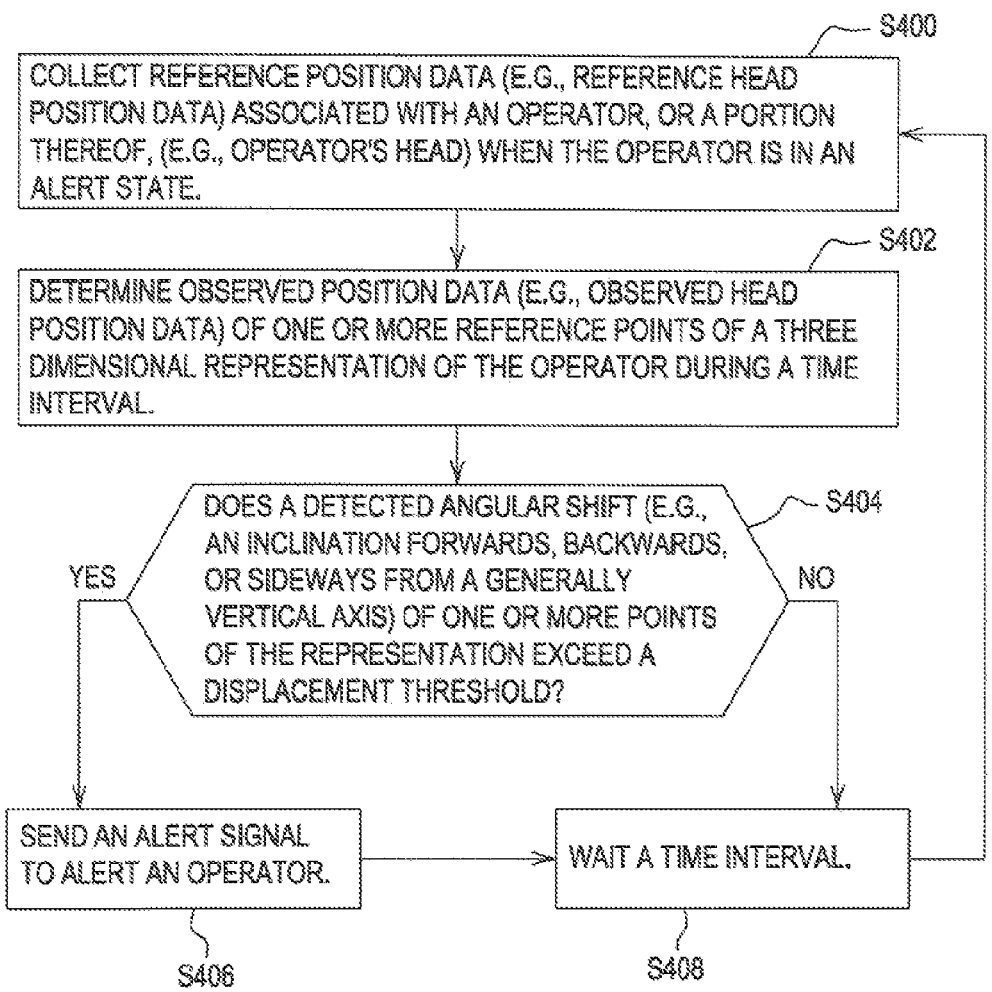
FIG. 5 is a flow chart of a second embodiment of a method for detecting the alertness of an operator.

FIG. 5 is a flow chart of a method for determining an alertness of an operator of a vehicle or machine. The method of FIG. 5 begins in step S400.

In step S400, an image collection system 15 or an imaging system collects reference position data (e.g., reference head position data) associated with an operator, or a portion thereof, (e.g., an operator's head) when the operator is in an alert state. An alert state refers to one in which the operator is conscious, awake, mentally aware, and/or attentive of the operation and control of the vehicle or machine.

The reference position data may be defined in accordance with various definitions that may be applied alternately or cumulatively. Under a first definition, the reference position data comprises the three dimensional coordinates (e.g., Cartesian or polar coordinates) associated with an operator, or a portion thereof. Under a second definition, the reference position data comprises the three dimensional coordinates associated with one or more reference points (e.g., first reference point (131) and a second reference point (133) of FIG. 4A) of the operator head 48. Under a third definition, the reference position data comprises a reference axis defined by two reference points lying on a surface of the operator's head, and their respective three dimensional coordinates, when the operator is in an alert state.

In one embodiment, step S400 may be carried by executing the stereo vision process of step S199 (which was previously described in conjunction with FIG. 2) to create a three dimensional representation of the operator when the operator is in an alert state and selecting one or more reference points associated with the three dimensional representation.

In step S402, the image processor 20 or object position estimator 25 determines observed position data (e.g., observed head position data) of one or more reference points of a three dimensional representation of the operator during a time interval. The observed position data may be defined in accordance with various definitions that may be applied alternately or cumulatively. Under a first definition, the observed, position data comprises three dimensional coordinates (e.g., Cartesian or polar coordinates) of one or more reference points associated with an operator, or a portion thereof. Under a second definition, the observed position data may comprise the three dimensional coordinates associated with one or more reference points (e.g., first reference point (231 or 331) and a second reference point (233 or 333) of FIG. 4B or FIG. 4C) of the operator head 48. Under a third definition, the observed position data comprises a reference axis defined by two reference points lying on a surface of the operator's head, and their respective three dimensional coordinates.

In one embodiment, step S402 may be carried by executing the stereo vision process of step S199 to create a three dimensional representation of the operator when the operator is under observation to monitor the operator's alertness. Further, the image processor 20 or image position estimator 25 selects one or more reference points associated with the three dimensional representation as the observed position data.

In step S404, the analyzer 32 or evaluator 36 determines whether a detected angular shift (e.g., an inclination, forwards, backwards, or sideways from a generally vertical axis) of one or more of points of the representation exceed a displacement threshold. For example, the analyzer 32 or evaluator 36 determines whether a defected angular shift (e.g., an inclination, forwards, backwards, or sideways from a generally vertical axis) from the reference position data to the observed position data of one or more of points of the representation exceed a displacement threshold. A displacement threshold refers to a distance that exceeds a minimum distance or an angle that exceeds a critical angle (e.g., first critical angle 235 of FIG. 4B or second critical angle 335 of FIG. 4C) or minimum angle. For example, where the reference points define an observed axis, the detected angular shift may represent an inclination forwards, backwards or sideways of the observed axis with respect to a generally vertical axis by at least a critical angle.

If the analyzer 32 or evaluator 36 determines that the detected angular shift exceeds a displacement threshold, the method continues with step S406. However, if the analyzer 32 or evaluator 36 determines that the detected angular shift does not exceed a displacement threshold, the method continues with step S408.

In step S406, an analyzer 32 or an alert device 40 sends an alert signal to alert an operator. For example, the alert device 40 generates an audible tone or alarm to wake or otherwise alert the operator. After step S406, the method may continue with step S408, for example.

In step S408, the image collection system 15 waits a time interval (e.g., a sampling interval) prior to returning to step S400 to collect reference position data.

Figure 6:
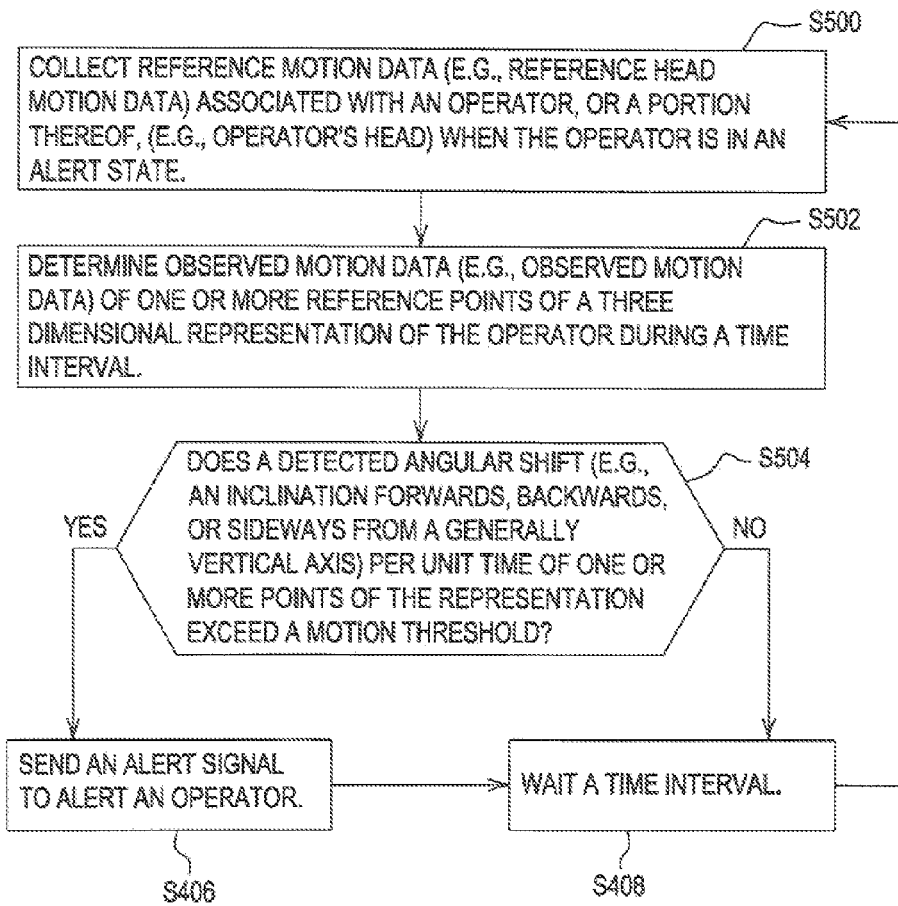
FIG. 6 is a flow chart of a third embodiment of a method for detecting the alertness of an operator.

FIG. 6 is a flow chart of a method for determining an alertness of an operator. The method of FIG. 6 begins in step S500.

In step S500, an image collection system 15 or an imaging system collects reference motion data (e.g., reference head motion data) associated with an operator, or a portion thereof, when the operator is in an alert state. For example, the image collection system 15 or the imaging system collects motion data as at least two three dimensional representations of an operator, or a portion thereof, over a first time period via stereo vision processing.

The reference motion data may be defined in accordance with various definitions that may be applied alternately or cumulatively. Under a first definition, the reference motion data may comprise movement associated with the three dimensional coordinates of one or more reference points associated with an operator, or a portion thereof. Under a second definition, the reference motion data comprises movement associated with a reference axis defined by two reference points lying on a surface of the operator's head, and their respective three dimensional coordinates, when the operator is in an alert state.

In one embodiment, step S500 may be carried by executing the stereo vision process of step S199 (which was previously described in conjunction with FIG. 2) to create multiple three dimensional representations of the operator at corresponding times when the operator is in an alert state and selecting one or more reference points associated with the three dimensional representation. The clock 31 or object motion estimator 31 may track the elapsed time (e.g., first time period) between the multiple three dimensional images to derive reference motion data characteristic of an operator in an alert state.

In step S502, the image processor 20 or object position estimator 25 determines observed motion data (e.g., observed head motion data) of one or more reference points of a three dimensional representation of the operator during a time interval. For example, the image processor 20 or object position estimator 25 determines observed motion data as at least two three dimensional representations of an operator, or a portion thereof, over a second time period via stereo vision processing.

The observed motion data may be defined in accordance with various definitions that may be applied alternately or cumulatively. Under a first definition, the observed motion data comprises movement associated with three dimensional coordinates of one or more reference points associated with an operator, or a portion thereof. Under a second definition, the observed motion data comprises movement associated with a reference axis defined by two reference points lying on a surface of the operators head, and their respective three dimensional coordinates.

In one embodiment, step S502 may be carried by executing the stereo vision process of step S198 (which was previously described in conjunction with FIG. 2) to create multiple three dimensional representations of the operator at corresponding times when the operator is operating the vehicle and selecting one or more reference points associated with the three dimensional representation. The clock 31 or object motion estimator 31 may track the elapsed time (e.g., second time period) between the multiple three dimensional images to derive observed motion data of the operator while operating the vehicle.

In step S504, the analyzer 32 or evaluator 36 determines whether a detected angular shift (e.g., an inclination, forwards, backwards, or sideways from a generally vertical axis) per unit time of one or more reference points of the representation exceeds a motion threshold. For example, the analyzer 32 or evaluator 36 determines whether a detected angular shift (e.g., an inclination, forwards, backwards, or sideways from a generally vertical axis) from the reference motion data to the observed motion data of one or more of points of the representation exceed a motion threshold. A motion threshold refers to a distance that exceeds a minimum distance or an angle that exceeds a minimum or critical angle per unit time or over an elapsed time period of known duration. For example, where the reference points define an observed axis, the detected angular shift may represent an inclination forwards, backwards or sideways of the observed axis with respect to a generally vertical axis by at least a critical angle over an elapsed time period.

In an alternate embodiment, the motion threshold may be defined as a lack of motion over an elapsed time period (or minimal displacement over an elapsed time period) that is correlated to or indicative of an operator in a potentially inattentive state or degraded alertness.

If the analyzer 32 or evaluator 36 determines that the detected angular shift exceeds a motion threshold, the method continues with step S406. However, if the analyzer 32 or evaluator 36 determines that the detected angular shift does not exceed a motion threshold, the method continues with step S408.

In step S408, the image collection system 15 waits a time interval (e.g., a sampling interval) prior to returning to step S500 to collect reference motion data. After step S408, the method may continue with step S408, for example.

Figure 7:
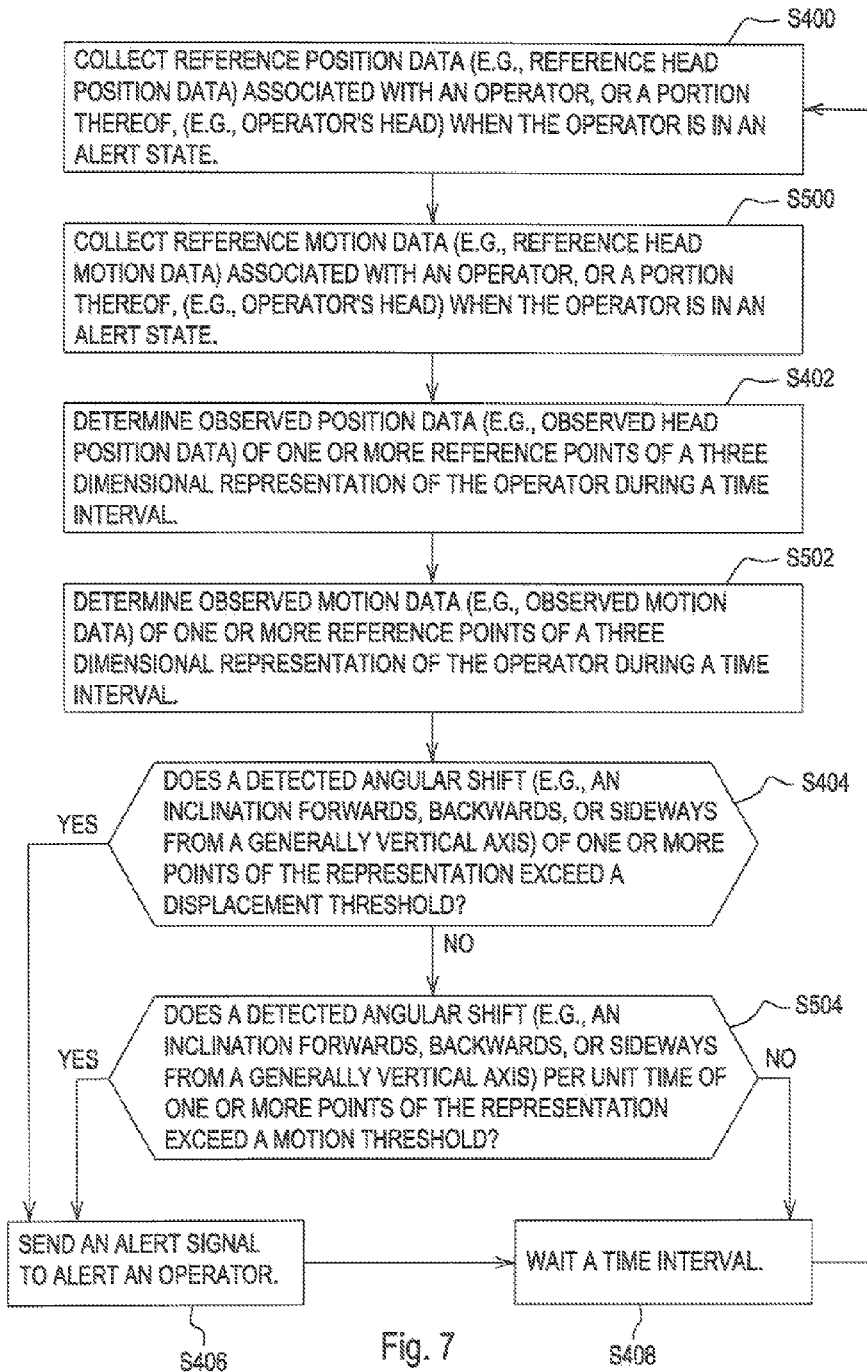
FIG. 7 is a flow chart of a fourth embodiment of a method for detecting the alertness of an operator.

FIG. 7 is a flow chart of a method for determining an alertness of an operator. Like reference numbers in FIG. 7 and FIG. 5, or in FIG. 7 and FIG. 8, indicate like steps or procedures. The method of FIG. 7 begins in step S400.

In step 3400, an image collection system 15 or an imaging system collects reference position data (e.g., reference head position data) associated with an operator, or portion thereof, (e.g., an operator's head) of a vehicle when the operator is in an alert state.

In step S500, an image collection system 15 or an imaging system collects reference motion data (e.g., reference head motion data) associated with an operator, or portion thereof, (e.g., an operator's head) when the operator is in an alert state.

In step S402, the image processor 20 or object position estimator 25 determines observed position data (e.g., observed head position data) of one or more reference, points of a three dimensional representation of the operator during a time interval.

In step S502, the image processor 20 or object position estimator 25 determines observed motion data (e.g., observed head motion data) of one or more reference points of a three dimensional representation of the operator during a time interval.

in step S404, the analyzer 32 or evaluator 36 determines whether a detected angular shift (e.g., an inclination, forwards, backwards, or sideways from a generally vertical axis) of one or more of points of the representation exceed a displacement threshold. A displacement threshold refers to a distance that exceeds a minimum distance or an angle that exceeds a critical angle or minimum angle. If the analyzer 32 or evaluator 36 determines that the detected angular shift exceeds, a displacement threshold, the method continues with step S406. However, if the analyzer 32 or evaluator 36 determines that the detected angular shift does not exceed a displacement threshold, the method continues with step S504.

In step S406, an analyzer 32 or an alert device 40 sends an alert signal to alert an operator. For example, the alert device 40 generates an audible tone or alarm to wake or otherwise alert the operator.

In step S504, the analyzer 32 or evaluator 36 determines whether a detected angular shift (e.g., an inclination, forwards, backwards, or sideways from a generally vertical axis) of one or more of points of the representation exceed a motion threshold. A motion threshold refers to movement exceeding a minimum distance within a time window, or movement exceeding an angular displacement within a time window. For example, the angular displacement means a critical angle (e.g., first critical angle 235 of FIG. 4B or second critical angle 335 of FIG. 4C) or minimum angle. If the analyzer 32 or evaluator 36 determines that the detected angular shift exceeds a motion threshold, the method continues with step S406. However, if the analyzer 32 or evaluator 36 determines that the detected angular shift does not exceed a motion threshold, the method continues with step S408.

In step S408, the image collection system 15 waits a time interval (e.g., a sampling interval) prior to returning to step S400 to collect reference position data.

Figure 8:
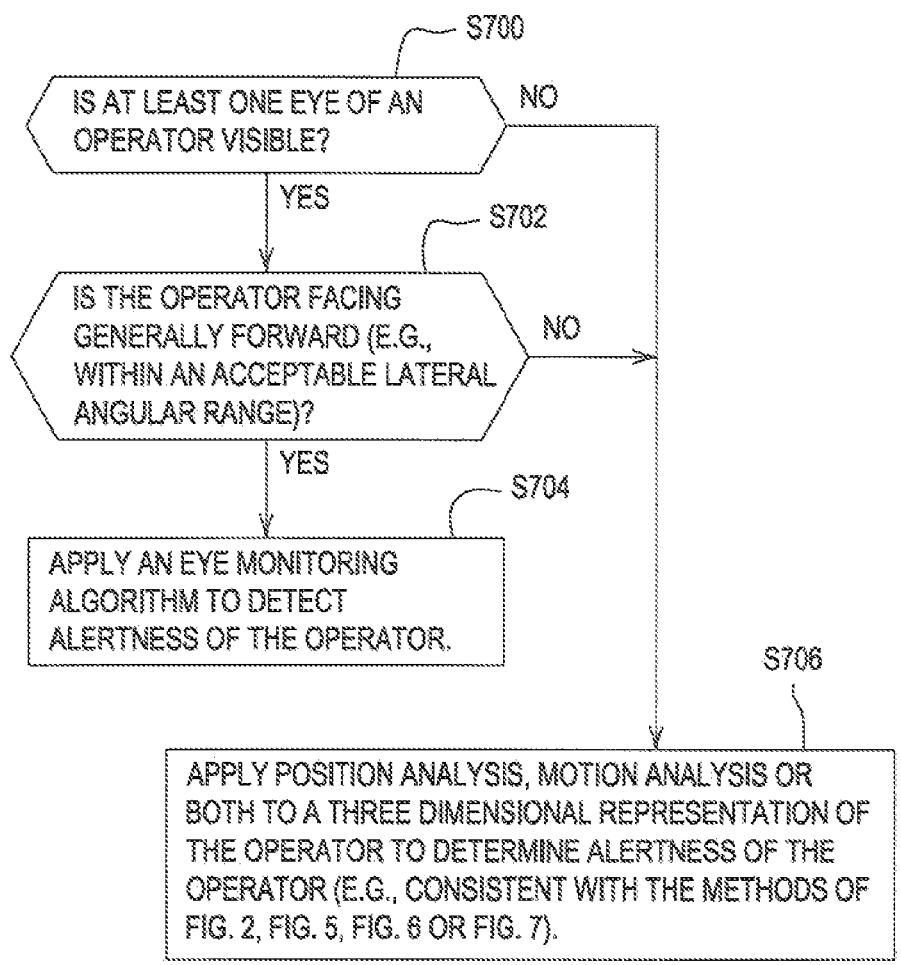
FIG. 8 is a flow chart of a fifth embodiment of a method for detecting the alertness of an operator.

FIG. 8 is a flow chart of another method for determining an alertness of an operator.

In step S700, an image collection system 15 determines if at least one eye of an operator is visible, if at least one eye of the operator is visible, the method continues with step 3702. However, if no eyes of the operator are visible, the method continues with step S708.

In Step S702, the image collection system 15 determines whether or not the operator is generally facing forward (e.g., in a cab or cockpit of the vehicle). Here, forward refers to the toward direction of travel of the vehicle or the front of the vehicle. The operator may be regarded as facing forward if the operator is within a certain lateral angular range (e.g., plus or minus 40 degrees) of absolute forward or the forward direction of travel of the vehicle. If the operator is generally facing forward, the method continues with step S704. However, if the operator is not facing forward, the method continues with step S708.

In step S704, the eye monitoring algorithm and/or equipment detects alertness of an operator. The eye monitoring algorithm and/or equipment may determine one or more of the following: (1) whether one or both eyes of the operator are open or closed, (2) the rate at which the operator blinks, (3) the ratio or percentage of eye closure (PERCLOS) over a time period, and (4) whether the movement of the pupil of the operator's eye is consistent with alertness. For example, whether or not one or both of the operator eyes are open may be determined by the image processor 20 applying color differentiation (e.g., open eye colors versus closed eye colors) in the region of the operator's eye. The use of such eye related data may require filtering to remove the effects of eye movements associated with cognitive demands of the task and brightness of the ambient lighting that might otherwise be perceived as an indicator of alertness or inattentiveness of the operator. Any commercially available eye monitoring algorithms and/or equipment may be used to execute step S704.

In step S706, which may be carried out after step S700 or S702, the imaging system or image processor 20 applies position analysis, motion analysis, or both to a three dimensional representation of the operator (e.g., the operator's head, head and neck region, or bust) to determine alertness of the operator. Step S706 may be carried out in accordance with various methods, which may be applied individually, cumulatively, or collectively. Under a first method, the method if FIG. 5 may be applied to carry out step S706. Under a second method, the method of FIG. 6 may be applied to carry out step S706. Under a third method, the method of FIG. 7 may be applied to carry out step S706.

Under a fourth method, the image collection system 15 or the system (11 or 111) collects reference position data associated with an operator, or a portion thereof, when the operator is in an alert state; the image processor 20 or analyzer system 32 determines observed position data of one or more points of a three dimensional representation of the operator during a time interval; and an alert device 40 or analyzer system 32 sending an alert signal to alert the operator if a detected angular shift of one or more points of the representation exceed a displacement threshold. Pursuant to the fourth method, the image processor 20 or the three dimensional image former 23 establishes a three dimensional representation of an operator via stereo vision processing, which may comprise gathering a pair of raw stereo scene images of the operator, or a portion thereof, from spatially offset perspectives; combining the raw stereo scene images to produce a disparity map image that represents a disparity between the raw stereo scene images; and creating a three dimensional representation of the operator, or a portion thereof, based on the disparity map and the raw stereo scene images.

Under a fifth method, the image collection system 15 or the system (11 or 111) collects reference motion data associated with an operator, or a portion thereof, when the operator is in an alert state; the image processor 20 or analyzer system 32 determines observed motion data of one or more points of a three dimensional representation of the operator during a time interval; and an alert device 40 or analyzer system 32 sending an alert signal to alert the operator if a detected angular shift of one or more points of the representation exceed a motion threshold. Pursuant to the fifth method, the image processor 20 or the three dimensional image former 23 establishes multiple three dimensional representations of an operator via stereo vision processing, which may comprise gathering a pair of raw stereo scene images of the operator, or a portion thereof, from spatially offset perspectives; combining the raw stereo scene images to produce a disparity map image that represents a disparity between the raw stereo scene images; and creating one or more three dimensional representations of the operator, or a portion thereof, based on the disparity map and the raw stereo scene images.

Although the operator primarily refers to a driver of a vehicle, any embodiment of the system and method may be extended to the operator of a machine, the operator of electronic equipment, or the operator other equipment. The system and method for detecting operator alertness is well suited for monitoring operator alertness of operators that wear eyeglasses or sunglasses. Further, the system and method for detecting operating alertness may be applied to vehicle configurations or tasks where the operator lends not to face forward in a vehicle at all times during normal operation (e.g., certain construction equipment, agricultural equipment, or mining equipment).

Having described the preferred embodiment, it will become apparent that various modifications can be made without departing from the scope of the invention as defined in the accompanying claims.

We claim:

1. A method for detecting operator alertness of an operator of a vehicle or machine, the method comprising:
    collecting reference position data associated with the operator when the operator is in an alert state, wherein the collecting reference position data comprises creating a three dimensional representation of the operator, or a portion thereof, via stereo vision processing;
    determining observed position data of one or more reference points of the three dimensional representation of the operator, or the portion thereof, during a time interval; and
    sending an alert signal to alert the operator if a detected angular shift of the one or more reference points of the three dimensional representation exceed a displacement threshold.

2. The method according to claim 1 wherein the determining observed position data comprises creating a three dimensional representation of the operator, or the portion thereof via the stereo vision processing.

3. The method according to claim 1 wherein the collecting reference position data further comprises:
    gathering a pair of raw stereo scene images of the operator, or the portion thereof, from spatially offset perspectives;
    identifying respective operator-related image data in the gathered raw stereo scene images;
    combining at least one of (i) the raw stereo scene images together with each other and (ii) the operator-related image data together with each other to produce a disparity map image that represents a disparity between the raw stereo scene images; and
    creating a three dimensional representation of the operator, or the portion thereof, based on the disparity map and the raw stereo scene images.

4. The method according to claim 1 wherein the determining observed position data further comprises:
    gathering a pair of raw stereo scene images of the operator, or the portion thereof, from spatially offset perspectives;
    identifying respective operator-related image data in the gathered raw stereo scene images;
    combining at least one of the (i) raw stereo scene images together with each other and (ii) the operator-related image data together with each other to produce a disparity map image that represents a disparity between the raw stereo scene images; and
    creating a three dimensional representation of the operator, or the portion thereof, based on the disparity map and the raw stereo scene images.

5. The method according to claim 1 wherein the reference position data comprises three dimensional coordinates of one or more reference points associated with the operator, or the portion thereof.

6. The method according to claim 1 wherein the reference position data comprises a reference axis defined by two reference points lying on a surface of the operator's head, and their respective three dimensional coordinates, when the operator is in an alert state.

7. The method according to claim 1 wherein the observed position data comprises three dimensional coordinates of one or more reference points associated with the operator, or the portion thereof.

8. The method according to claim 1 wherein the observed position data comprises a reference axis defined by two reference points lying on a surface of the operator's head, and their respective three dimensional coordinates.

9. The method according to claim 1 wherein the detected angular shift represents an inclination forwards, backwards, or sideways of one or more reference points.

10. The method according to claim 1 wherein the reference points define an observed axis and wherein the detected angular shift represents an inclination forwards, backwards or sideways of the observed axis with respect to a generally vertical axis by at least a critical angle.

11. A system for detecting operator alertness of an operator of a vehicle or machine, the system comprising:
    a stereo vision image collection system for collecting reference position data associated with the operator when the operator is in an alert state, wherein the reference position data comprises a three dimensional representation of the operator, or a portion thereof, created via stereo vision processing by the stereo vision image collection system;
    an image processor for determining observed position data of one or more reference points of the three dimensional representation of the operator, or the portion thereof, during a time interval; and
    an analyzer for sending an alert signal to alert the operator if a detected angular shift of the one or more reference points of the three dimensional representation exceed a displacement threshold.

12. The system according to claim 11 wherein the image processor further comprises an image former for creating a three dimensional representation of the operator, or the portion thereof.

13. The system according to claim 11 further comprising:
    a plurality of imaging units for gathering a pair of raw stereo scene images of the operator, or the portion thereof, from spatially offset perspectives;
    an image segmenter for identifying respective operator-related image data in the gathered raw stereo scene images;
    an image disparity module for combining at least one of (i) the raw stereo scene images together with each other and (ii) the operator-related image data together with each other to produce a disparity map image that represents a disparity between the raw stereo scene images; and
    an image former for creating a three dimensional representation of the operator, or the portion thereof, based on the disparity map and the raw stereo scene images.

14. The system according to claim 11 wherein the reference position data comprises three dimensional coordinates of one or more reference points associated with the operator, or the portion thereof.

15. The system according to claim 11 wherein the observed position data comprises three dimensional coordinates of one or more reference points associated with the operator, or the portion thereof.

16. The system according to claim 11 wherein the reference position data comprises a reference axis defined by two reference points lying on a surface of the operator's head, and their respective three dimensional coordinates, when the operator is in an alert state.

17. The system according to claim 13 wherein the observed position data comprises three dimensional coordinates of one or more reference points associated with the operator, or the portion thereof.

18. The system according to claim 11 wherein the observed position data comprises a reference axis defined by two reference points lying on a surface of the operator's head, and their respective three dimensional coordinates.

19. The system according to claim 11 wherein the detected angular shift represents an inclination forwards, backwards, or sideways of one or more reference points.

20. The system according to claim 11 wherein the reference points define an observed axis and wherein the detected angular shift represents an inclination forwards, backwards or sideways of an observed axis with respect to a generally vertical axis by at least a critical angle.

* * * * *